US00PP20937P2

(12) United States Plant Patent
Tristram

(10) Patent No.: US PP20,937 P2
(45) Date of Patent: Apr. 20, 2010

(54) ***DIGITALIS* PLANT NAMED 'WALDIGONE'**

(50) Latin Name: *Obscura×ambigua*
Varietal Denomination: WALDIGONE

(76) Inventor: David Ralph Tristram, Yapton Lane, Walberton, Arundel, West Sussex (GB) BN18 0AS ( * ) Notice: Subject to any disclaimer, the term of this patent is extended or adjusted under 35 U.S.C. 154(b) by 0 days.

(21) Appl. No.: 12/321,699

(22) Filed: Jan. 23, 2009

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Susan B McCormick Ewoldt

(57) ABSTRACT

A new cultivar of *DIGITALIS* plant named "WALDIGONE" that is characterized by short, upright, multi-stemmed habit, dense and bushy plant form and flowers which are colored yellow with tinges of orange and red and whose lower lip petal projects approximately 6 mm beyond the other petals. In combination these traits set 'WALDIGONE' apart from all other existing varieties of *DIGITALIS* known to the inventor.

2 Drawing Sheets

Genus: *DIGITALIS.*

Species: *obscura×ambigua.*

Denomination: 'WALDIGONE'.

BACKGROUND OF THE INVENTION

The present Invention relates to a new and distinct cultivar of *Digitalis* plant, commonly known as foxglove and botanically known as *Digitalis obscura×Digitalis ambigua*, and hereinafter referred to by the cultivar name 'WALDIGONE'.

'WALDIGONE' is a product of a planned breeding program conducted by the Inventor in Walberton, Sussex, United Kingdom. The objective of the breeding program was to create free-flowering new *Digitalis* cultivars with numerous flowers with attractive coloration.

'WALDIGONE' originated from a cross-pollination made by the Inventor in 2001 of the species *Digitalis obscura* as the female, or seed, parent and *Digitalis ambigua* as the male, or pollen, parent. 'WALDIGONE' was discovered and selected by the Inventor in 2003 as a single flowering plant in a controlled environment in Walberton, Sussex, United Kingdom.

Plants of 'WALDIGONE' can be compared to the female parent, *Digitalis obscura* as follows: Compared to plants of the female parent, *Digitalis obscura*, plants of 'WALDIGONE' have broader leaves, and flowers which are more yellow in color.

Plants of 'WALDIGONE' can be compared to the male parent, *Digitalis ambigua*, as having narrower and more glabrous leaves and flowers which are more orange in color.

Plants of ' WALDIGONE' can be compared to plants of the *Digitalis* cultivar 'Spice Island' (U.S. Plant Pat. No. 17,849) as follows: Plants of 'WALDIGONE' differ primarily from plants of 'Spice Island' in being less tall and quicker to come into flower. In addition, flowers of 'Spice Island' have much longer sepals and more projecting lower lips than flowers of WALDIGONE.

Asexual reproduction of 'WALDIGONE' was first accomplished by the inventor in 2003, using the method of tissue culture. Since that time, the distinguishing features of 'WALDIGONE' have been found to be are stable and to reproduce true to type in successive generations of asexual reproduction.

SUMMARY OF THE INVENTION

The following traits have been repeatedly observed and represent the characteristics of 'WALDIGONE'. These traits in combination distinguish this cultivar from all other commercial varieties known to the inventor. 'WALDIGONE' has not been tested under all possible conditions and phenotypic differences may be observed with variations in environmental, climatic and cultural conditions, however, without any variance in genotype.

1. Plants if 'WALDIGONE' exhibit short, upright, multi-stemmed habit.
2. Plants if 'WALDIGONE' exhibit short internodes and a dense and bushy plant form.
3. The flowers of 'WALDIGONE' are colored yellow flowers with tinges of orange and red.
4. The lower lip petal of a flower of WALDIGONE' projects approximately 6 mm beyond the other petals.

BRIEF DESCRIPTION OF THE DRAWINGS

The accompanying color drawings illustrate the overall appearance of 'WALDIGONE' showing colors as true as it is reasonably possible to obtain in colored reproductions of this type. Colors in the drawings may differ slightly from the color values cited in the detailed botanical description which accurately describe the actual colors of 'WALDIGONE'.

The illustrated plants have been grown in 1.5-litre container plants and are approximately one and a half years old. The plants have been grown out of doors in Walberton, Sussex, United Kingdom.

Figure 1:
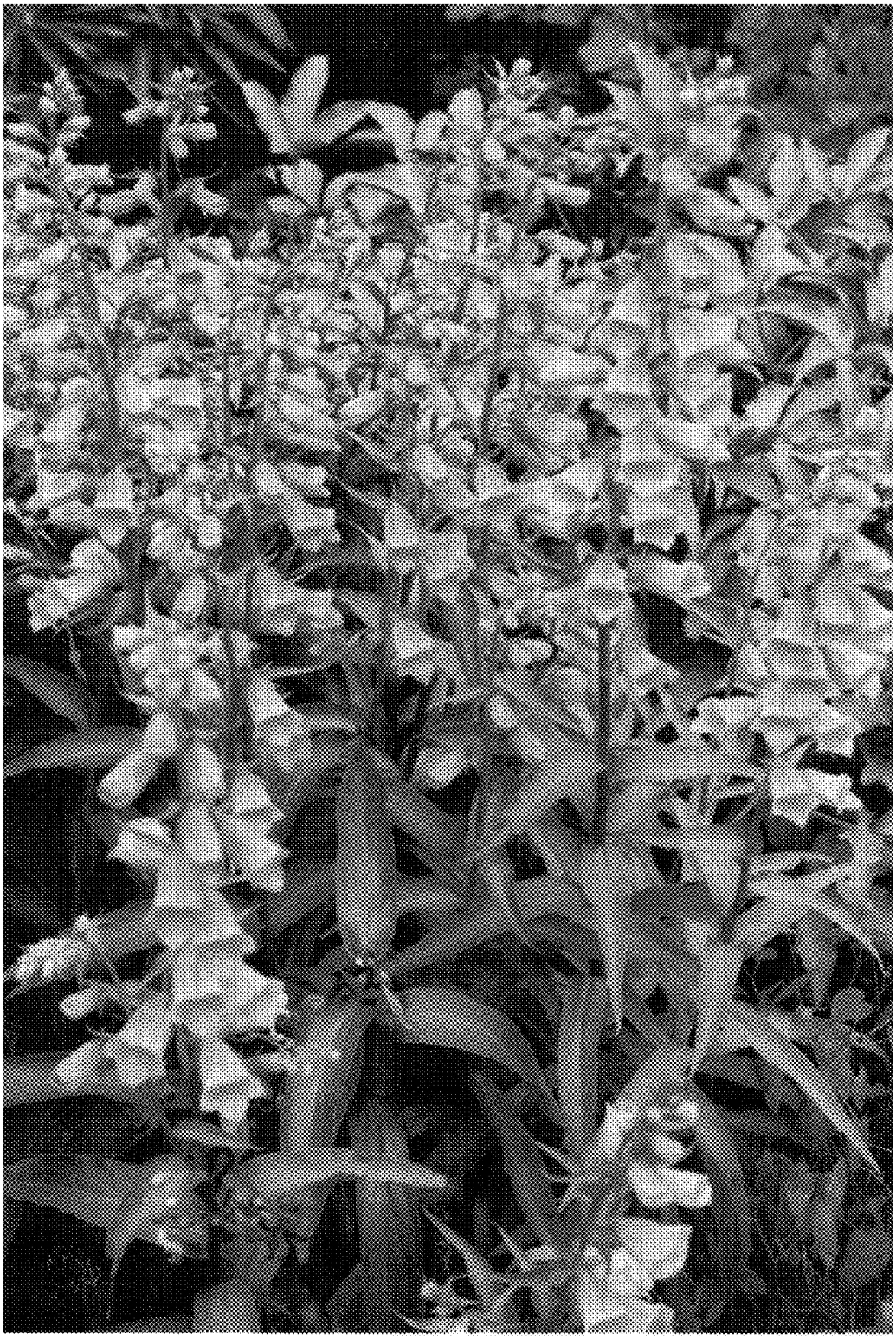

The drawing labeled as FIG. 1 depicts flowering plants of 'WALDIGONE'.

Figure 2:
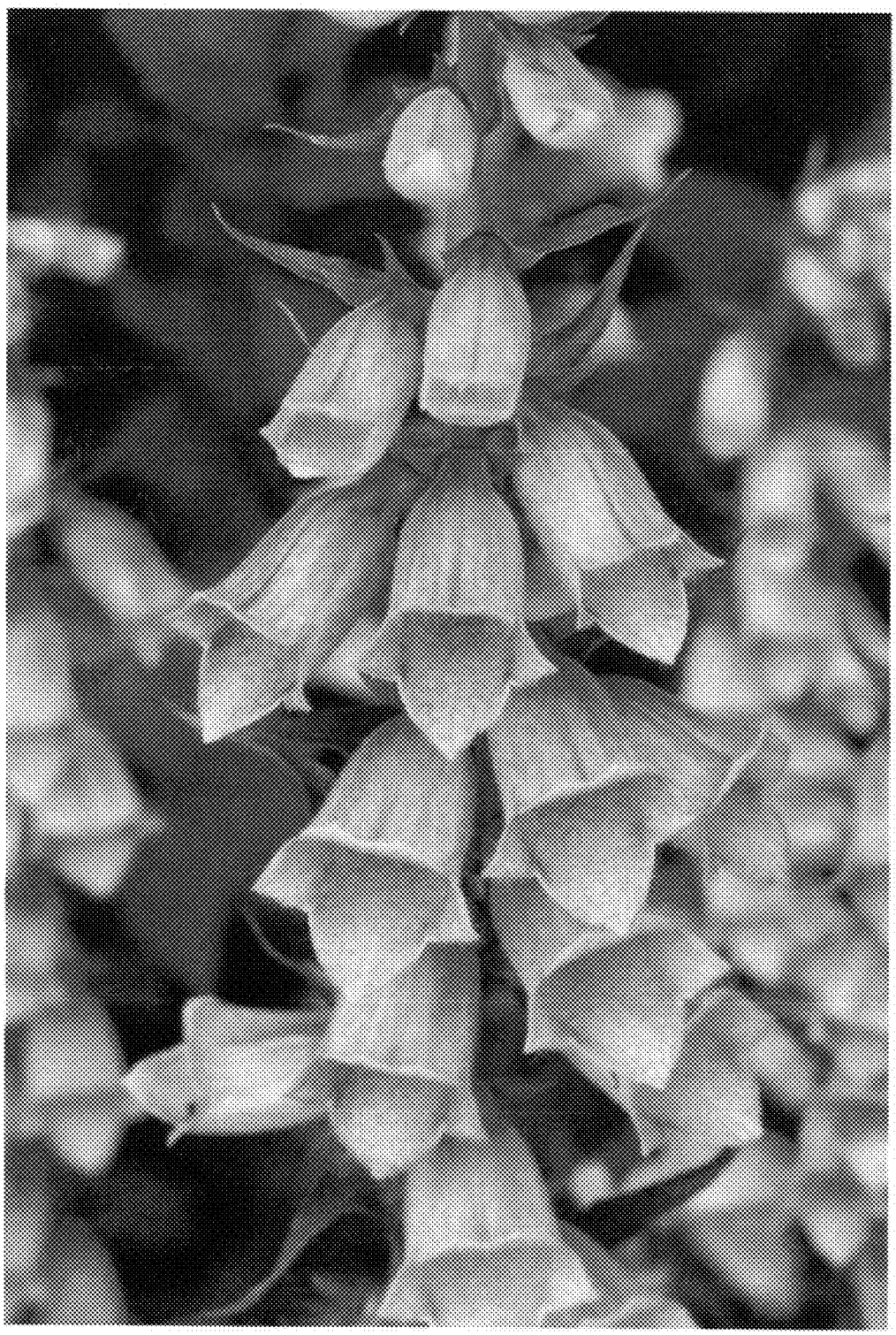

The drawing labeled as FIG. 2 is a close-up view of a typical flower raceme of 'WALDIGONE'.

DETAILED BOTANICAL DESCRIPTION

The following is a detailed description of the new cultivar 'WALDIGONE'. Data was collected by the inventor in spring and summer from 1.5-litre container plants in spring which were approximately one and a half years old. The plants have been grown out of doors in Walberton, Sussex, United Kingdom. The color determinations are in accordance with the 1966 Edition of The Royal Horticultural Society Colour Chart of The Royal Horticultural Society, London, England, except where general color terms of ordinary dictionary significance are used.

Botanical classification: Genus, species: *Digitalis obscura*× *Digitalis ambigua*. Denomination: 'WALDIGONE'.

Parentage:

*Female, or seed, parent.*—*Digitalis obscura.*

*Male, or pollen, parent.*—*Digitalis ambigua.*

Propagation method: Tissue culture.

Root description: Fine; freely branching.

Disease/pest resistance: Plants of 'WALDIGONE' have not been noted to be resistant to pathogens and pests common to *Digitalis*.

Hardiness: Plants of 'WALDIGONE' have been observed to be hardy to USDA Zone 5.

Plant description:

Form: Perennial. Upright growing and compact plant habit.

Branching: Freely basal branching with about five to ten flowering stems per plant.

Habit: Dense and bushy plant habit; moderately vigorous growth habit.

Flowering: Up to 30 flowers arranged on crowded terminal raceme.

Plant height: Ranges between 45 cm and 60 cm.

Plant width: Ranges between 20 cm and 30 cm.

Stem description:

*Length* (*excluding inflorescence*).—20 cm.

*Diameter.*—3 mm–5 mm.

*Internode length.*—2 cm–3 cm.

*Strength.*—Moderate.

*Aspect.*—Erect.

*Texture.*—Smooth, glabrous.

*Color.*—144A.

Foliage description:

*Arrangement.*—Alternate, simple.

*Quantity per stem.*—5–10.

*Length.*—5 cm to 15 cm.

*Width.*—1.5 cm to 3.5 cm.

*Shape.*—Lanceolate.

*Apex.*—Apiculate.

*Base.*—Clasping stem.

*Margin.*—Simple or very slightly serrate.

*Texture, upper and lower surfaces.*—Smooth, glabrous.

*Venation pattern.*—Pinnate.

*Color.*—Developing foliage, upper surface: Closest to 137B. Developing foliage, lower surface: Closest to 137C. Fully expanded foliage, upper surface: Closest to 139A. Fully expanded foliage, lower surface: 138A. Venation, upper surface: 137A. Venation, lower surface: 138B.

*Petiole.*—None. Leaves sessile, stem-clasping.

Flower description:

*Flower arrangement and shape.*—Single bilabiate campanulate flowers closely spaced, about 1 cm apart, on upright terminal racemes; flowers face mostly outward and tend towards one side. Freely flowering habit, about 15–30 flowers per raceme.

*Natural flowering season.*—Continuous flowering during the summer (June through July) in the United Kingdom.

*Flower longevity on the plant.*—Individual flowers last about ten days on or off the plant. Flowers not persistent.

Flower buds:

*Length.*—About 1.5 cm.

*Diameter.*—About 5 mm.

*Shape.*—Ovoid.

*Color.*—Upper surface 164B, lower surface 160A.

Inflorescence size:

*Length.*—About 30 cm.

*Diameter.*—About 6 cm.

Flowers:

*Length.*—About 3.5 cm.

*Width.*—About 2.2 cm.

*Depth* (*height*).—About 1.5 cm.

*Fragrance.*—None.

Petals:

*Arrangement.*—Campanulate; five petals fused, bottom one forming projecting lower lip.

*Shape.*—Fused to become campanulate.

*Length, upper petals.*—About 2.5 cm.

*Length, lower lip petal.*—About 3 cm–3.5 cm.

*Width, lower lip petal.*—About 1.5 cm.

*Apex, lower lip petal.*—Cuspidate.

*Margin.*—Entire.

*Texture.*—Outer surface pubescent, inner surface hirsute.

*Color.*—Upper petals: When opening, upper surface: 20B blushed with about 173B. When opening, lower surface: 11A. Fully opened, upper surface: 20B, venation close to 173B. Fully opened, lower surface: 11A Lower lip petal: When opening, upper surface 11A, lower surface 11B. Fully opened, upper surface: 21A; venation 173B. Fully opened, lower surface: 20B; venation close to 173B.

Sepals:

*Arrangement/quantity per flower.*—Five, not fused.

*Length.*—About 6 mm.

*Width.*—About 2 mm–3 mm.

*Shape.*—Lanceolate to narrowly triangular.

*Apex.*—Acute.

*Margin.*—Entire.

*Texture, upper and lower surfaces.*—Slightly pubescent.

*Color, upper and lower surfaces.*—137D.

Peduncles:

*Length.*—About 3 cm–6 cm.

*Diameter.*—About 2 mm–5 mm.

*Aspect.*—Erect.

*Strength.*—Strong.

*Color.*—144B.

Pedicels:

*Length.*—About 5 mm.

*Diameter.*—About 1.5 mm.

*Strength.*—Moderate.

*Color.*—137D.

Reproductive organs:

*Stamens.*—Quantity per flower: Four.

*Filament length.*—About 1 cm.

*Filament color.*—20C.

*Anther shape.*—Reniform.

*Anther length.*—About 2 mm.

*Anther color.*—20B.

*Pollen amount.*—Moderate.

*Pollen color.*—20D.

*Pistils.*—Quantity per flower: One.

*Pistil length.*—About 2 cm.

*Stigma color.*—20D.

*Style length.*—About 1 cm.

*Style color.*—20D.

*Ovary color.*—144A.

*Fruit/seeds.*—Fruit and seed development have not been observed.

I claim:

1. A new and distinct cultivar of *DIGITALIS* plant named 'WALDIGONE' as described and illustrated herein.

* * * * *